United States Patent [19]

Hargett

[11] 3,942,512

[45] Mar. 9, 1976

[54] PHARYNGEAL AND NASOPHARYNGEAL TREATMENT

[76] Inventor: Edgar R. Hargett, 466 Woodlawn Ave., Springfield, Ohio 45504

[22] Filed: Feb. 12, 1975

[21] Appl. No.: 549,179

Related U.S. Application Data

[62] Division of Ser. No. 362,791, May 22, 1973, Pat. No. 3,873,721.

[52] U.S. Cl..................... 128/1 R; 424/313; 424/56
[51] Int. Cl.².................... A61B 19/00; A01N 9/24
[58] Field of Search ............................. 424/49–59, 424/313; 128/1 R Primary Examiner—Richard L. Huff
Attorney, Agent, or Firm—Biebel, French & Bugg

[57] ABSTRACT

A mouthwash solution and method for treating both the lower and upper throat. The aqueous solution contains dioctyl sodium sulfosuccinate as the active ingredient. The treatment of the lower throat involves holding a small amount of the solution in the mouth for a short period of time. The treatment for the upper throat area is to hold a small amount of the solution in the mouth, lie down with the head back, swallow several times, and hold the head in position for a short period of time.

1 Claim, No Drawings

PHARYNGEAL AND NASOPHARYNGEAL TREATMENT

CROSS-REFERENCE TO RELATED APPLICATION

This application is a division of application Ser. No. 362,791, filed May 22, 1973, now U.S. Pat. No. 3,873,721.

BACKGROUND OF THE INVENTION

The present invention relates to pharyngeal and nasopharyngeal treatment and more particularly, to the use of an aqueous solution of dioctyl sodium sulfosuccinate for treating conditions of the mouth, tongue, throat, pharynx, larynx, nasopharynx and any of the structures that open into these areas.

There are a large number of mouthwashes on the market today which claim to have extraordinary bactericidal activity. There are also a number of treatments for the nasopharynx including nose drops, atomizer sprays, and devices to spray salt water irrigations into the upper throat area. None of these external treatments are truly effective in treating conditions of the nasopharynx, including postnasal drip, drainage, and catarrh.

The lytic properties of dioctyl sodium sulfosuccinate are also well known. For example, in U.S. Pat. No. 2,149,240, there is disclosed a vaginal preparation containing a sulfodicarboxylic acid ester. It is stated therein that esters of sulfodicarboxylic acids are effective in immobilizing microorganisms because of their wetting properties and their lytic power.

The wetting properties of the esters of sulfodicarboxylic acids also make them useful for a large number of other purposes. In U.S. Pat. Nos. 2,028,091 and 2,176,423 an enumeration of possible uses for such compounds is made, listing uses ranging from lubricants to emulsifying agents to coating compositions. Likewise, U.S. Pat. No. 2,316,234 discloses using such compounds at low concentrations for germicides, insect sprays, laundry work, and even personal use. In medically related fields, in addition to use as a vaginal preparation, it is known that dioctyl sodium sulfosuccinate will soften stools and, as disclosed in U.S. Pat. No. 2,917,431, may be used in enemas for the treatment of severe fecal impactions and lesser degress of constipation.

Although dioctyl sodium sulfosuccinate is well known as a wetting agent and for its lytic power, it is not believed ever to have been used to treat throat conditions.

SUMMARY OF THE INVENTION

In accordance with the present invention, there is provided an effective treatment for conditions of both the lower and upper throat areas.

In regard to the lower throat area, the quick and simple treatment involves the use of an aqueous solution of dioctyl sodium sulfosuccinate in the form of a mouth wash or gargle. Since the lytic power of dioctyl sodium sulfosuccinate is great, even at low concentrations, lysis of bacteria cells is effected in a matter of seconds. In addition, since dioctyl sodium sulfosuccinate is an effecting wetting agent, it penetrates the mucus and plaque, lowers the surface tension, and aids in removal of the bacteria carrying mucus. It also removes the coating from the tongue. The lower throat is treated by holding one teaspoonful, or approximately five cubic centimeters, of the solution in the mouth, and gargling lightly if desired, for about one minute.

For treatment of the upper throat, approximately half-a-teaspoon of solution (two cubic centimeters or less) is held in the mouth while lying down on the back on a bed with the head hanging over the edge of the bed so that the nostrils are pointing to the ceiling. By swallowing several times and holding the head in position for about one minute, the solution is carried to all parts and depths of the areas opening into the upper throat, including the sphenoid sinus and eustachian tubes. Again, this is believed to be due to the instant wetting action of the dioctyl sodium sulfosuccinate. Because of this effect, the solution may be used in this treatment as a vehicle to carry other drugs, such as cortisone, or X-ray contrast, media into the nasopharynx and adjacent areas.

In addition to the dioctyl sodium sulfosuccinate active ingredient, the aqueous solutions of the present invention may contain non-pharmacological components such as a flavoring, coloring and sweetner, as well as other drugs or X-ray contrast media. The dioctyl sodium sulfosuccinate is, however, the only essential ingredient. Up to 2.5 percent of dioctyl sodium sulfosuccinate (i.e., the saturation point of dioctyl sulfosuccinate in water) may be used, but the preferred strength is around 0.25 percent. However, dioctyl sodium sulfosuccinate is also effective in concentrations as low as 0.0001 percent and may be used in such strengths, if desired.

Accordingly, it is a primary object of the present invention to provide a mouthwash containing dioctyl sodium sulfosuccinate.

Another object of the invention is to provide a method for treating the lower throat with an aqueous solution of dioctyl sodium sulfosuccinate.

It is still a further object of this invention to provide a method for treating the upper throat with an aqueous solution of dioctyl sodium sulfosuccinate.

Other objects and advantages of the present invention will be apparent from the following description and the appended claims.

DESCRIPTION OF THE PREFERRED EMBODIMENTS

The solution of the present invention was prescribed as a treatment for the common infections of the areas of the upper and lower throat in more than 500 cases. Each patient used a 0.25 percent solution of dioctyl sodium sulfosuccinate from once to several times daily, with no bad effects, and almost universal improvement. Since dioctyl sodium sulfosuccinate is a known drug for use in softening stools, and even has been used in General Food Corporation's instant soft drink mix, Kool-Aid, to improve dissolvability, it can be ingested without any ill effects. In fact, over a pint of a 0.25 percent solution of dioctyl sodium sulfosuccinate can be swallowed without exceeding the amount of dioctyl sodium sulfosuccinate ordinarily prescribed for the treatment of constipation.

The present use of dioctyl sodium sulfosuccinate does not, however, involve intentional ingestion of the mouthwash solution, except to the extent a small amount is swallowed after the treatment. For example, in the treatment of the lower throat it is recommended that after holding approximately one teaspoonful in the mouth with the head back, th excess is spit out, and what is left in the mouth swallowed. This carries a small amount of the solution down past the larynx and helps control infection in this area of the lower throat.

Due to the lytic power of the dioctyl sodium sulfosuccinate, there is a rapid lysis and destruction of the bacteria cells contacted. In addition, the wetting action of the dioctylsodium sulfosuccinate causes it to penetrate the plaque and mucus. It breaks the surface tension and aids in removal of the affected mucus from the mouth, throat and tongue. Such a treatment not only helps control the infections present, as well as the halitosis which goes with them, but also has great value in aborting acute infections of the throat at their onset. Despite these functions, there is no deleterious action on the mucous membrane itself. Likewise, not many people are allergic to dioctyl sodium sulfosuccinate.

When the dioctyl sodium sulfosuccinate solution is to be used in this manner as a mouthwash, it may be desirable to add the customary mouthwash ingredients to the aqueous solutions in order to make it more pleasant tasting and smoother.

For example, any approved flavoring may be used including lemon, vanilla, peppermint, cherry, etc. If an alcohol component, such as isopropanol or ethanol, is added, it may contain one-half percent of a denaturing which serves as a flavoring. Typical ones include cinnamon oil, clove oil, eucalyptus oil, and wintergreen oil. A complete list of the approved flavorings is set forth in U.S. Pat. No. 3,639,563, which is specifically incorporated herein by reference. The amount of non-toxic alcohol added is customarily between 5 and 25 percent.

Additional possible components include approximately 0.01 percent of a coloring, up to 0.04 percent of a sweetner such as sodium saccharin, and up to 15 percent of glycerine, sorbitol, or propylene glycol to supply body to the mouthwash. The remainder of the solution is water.

As noted, dioctyl sodium sulfosuccinate is well tolerated by the mucous membrane of the throat areas, but it may sting slightly when in contact with the nasal mucosa of the anterior portion of the nose. For this reason, it is preferred to use a smaller amount of the solution (i.e., half-a-teaspoonful or less) when treating the upper throat than when treating the lower throat. The lesser quantities help prevent the solution from spreading as far as the anterior portion of the nasal passages.

While the methods and compositions herein described constitute preferred embodiments of the invention, it is to be understood that the invention is not limited to these precise methods and compositions, and that changes may be made therein without departing from the scope of the invention which is defined in the appended claims.

What is claimed is:

1. A method of treating conditions of the upper throat comprising:
    holding a small amount, approximately half-a-teaspoonful or less, of an aqueous 0.25% solution of dioctyl sodium sulfosuccinate in the mouth,
    lying down with the head back, swallowing several times,
    and holding head in position for approximately 1 minute.

* * * * *

UNITED STATES PATENT OFFICE
CERTIFICATE OF CORRECTION

Patent No. 3,942,512　　　　　　　　　　Dated March 9, 1976

Inventor(s) Edgar R. Hargett　　　　　　　PAGE 1 of 2

It is certified that error appears in the above-identified patent and that said Letters Patent are hereby corrected as shown below:

Column 1, line 46, "degress" should read -- degrees --.

Column 1, line 64, "effecting" should read -- effective --.

Column 2, line 4, "half-a-teaspoon" should read -- half-a-teaspoonful --.

Column 2, line 67, "th" should read -- the --.

Column 4, end of paragraph in line 4, insert the two paragraphs:

-- It should be noted, however, that a simple solution of dioctyl sodium sulfosuccinate in water is sufficient and is, in fact, preferable where allergic effects may arise from the additional components. The dioctyl sodium sulfosuccinate is the only essential active ingredient, although, as previously mentioned, other drugs such as cortisone compounds may be present. Using the solution as a vehicle to carry cortisone compounds or X-ray contrast media is important in the treatment of the upper throat area which is difficult to reach with ordinary solutions. The wetting properties of the dioctyl sodium sulfosuccinate

UNITED STATES PATENT OFFICE
CERTIFICATE OF CORRECTION

Patent No. 3,942,512    Dated March 9, 1976

Inventor(s) Edgar R. Hargett    PAGE 2 of 2

It is certified that error appears in the above-identified patent and that said Letters Patent are hereby corrected as shown below:

cause it to spread into the nasopharynx, eustachian tubes, sphenoid sinus and adjacent areas when used to treat the upper throat in the manner described herein. Thus, it is an effective means for carrying allergy medicines, such as cortisone compounds, or contrast media into these areas.

The treatment of the upper throat involves holding a small amount of the solution in the mouth, lying down on the back on a bed, couch, etc. with the head hanging over the edge so that the nostrils are pointing to the ceiling, swallowing several times, and holding the head in position about one minute. This is an effective method of controling post-nasal drip, drainage, and catarrh. Since it heals the upper throat and takes the inflammation out of this area, it allows other areas such as the anterior sinuses to drain more freely.

Signed and Sealed this

Fourteenth Day of December 1976

[SEAL]

Attest:

RUTH C. MASON
Attesting Officer

C. MARSHALL DANN
Commissioner of Patents and Trademarks